United States Patent [19]

Hatton et al.

[11] Patent Number: 4,660,414
[45] Date of Patent: Apr. 28, 1987

[54] PETROLEUM STREAM MONITORING MEANS AND METHOD

[75] Inventors: Gregory J. Hatton; David A. Helms; Thomas M. Williams, all of Houston, Tex.

[73] Assignee: Texaco Inc., White Plains, N.Y.

[21] Appl. No.: 775,073

[22] Filed: Sep. 12, 1985

[51] Int. Cl.⁴ .......................................... G01N 33/28
[52] U.S. Cl. ................................................ 73/61.1 R
[58] Field of Search ................ 73/61 R, 61.1 R, 19, 73/861.04, 200, 155

[56] References Cited

U.S. PATENT DOCUMENTS

| | | | |
|---|---|---|---|
| 3,498,112 | 3/1970 | Howard | 73/61.1 R |
| 3,525,258 | 8/1970 | Fowler et al. | 73/155 |
| 4,048,854 | 9/1977 | Herzl | 73/61.1 R |
| 4,144,754 | 3/1979 | Pitts, Jr. et al. | 73/861.02 |
| 4,168,627 | 9/1979 | Pichon | 73/195 |
| 4,215,567 | 8/1980 | Vleek | 73/61.1 R |
| 4,272,982 | 6/1981 | Arnold et al. | 73/861.02 |
| 4,282,760 | 8/1981 | Pitts, Jr. et al. | 73/861.02 |
| 4,429,581 | 2/1984 | Furmaga | 73/861.04 |
| 4,499,418 | 2/1985 | Helms et al. | 73/61.1 R |

Primary Examiner—Stewart J. Levy
Assistant Examiner—Hezron E. Williams
Attorney, Agent, or Firm—Robert A. Kulason; James J. O'Loughlin; Ronald G. Gillespie

[57] ABSTRACT

Apparatus and method for monitoring a petroleum stream includes stratifying the petroleum stream into substantially liquid and gas streams. Predetermined parameters of the stratified petroleum stream are sensed and signals are provided accordingly. A sample of the liquid stream of the stratified petroleum stream is taken and parameters of the sample stream are also sensed with representative signals provided by sensors. Circuitry provides signals representative of the water faction, the gas faction, and the oil faction of the petroleum stream in accordance with the signals from all of the sensors.

18 Claims, 2 Drawing Figures

PETROLEUM STREAM MONITORING MEANS AND METHOD

BACKGROUND OF THE INVENTION

1. Field of the Invention

The present invention relates to apparatus and methods for monitoring petroleum streams in general, and more particularly, for monitoring a crude oil petroleum stream.

2. SUMMARY OF THE INVENTION

Apparatus and method for monitoring a petroleum stream included stratifying the petroleum stream into substantially liquid and gas streams. Predetermined parameters of the stratified petroleum stream are sensed and signals are provided accordingly. A sample of the liquid stream of the stratified petroleum stream is taken and parameters of the sample stream are also sensed with representative signals provided by sensors. Circuitry provides signals representative of the water flow rate, the gas flow rate, and the oil flow rate of the petroleum stream in accordance with the signals from all of the sensors.

The object and advantages of the invention will appear more fully hereinafter, consideration of the detailed description which follows, taken together with the accompanying drawings, wherein one embodiment of the invention is illustrated by way of example. It is to be expressly understood, however, that the drawings are for illustration purposes only and are not to be constued as defining the limits of the invention.

Description of the Preferred Embodiment

Figure 1:
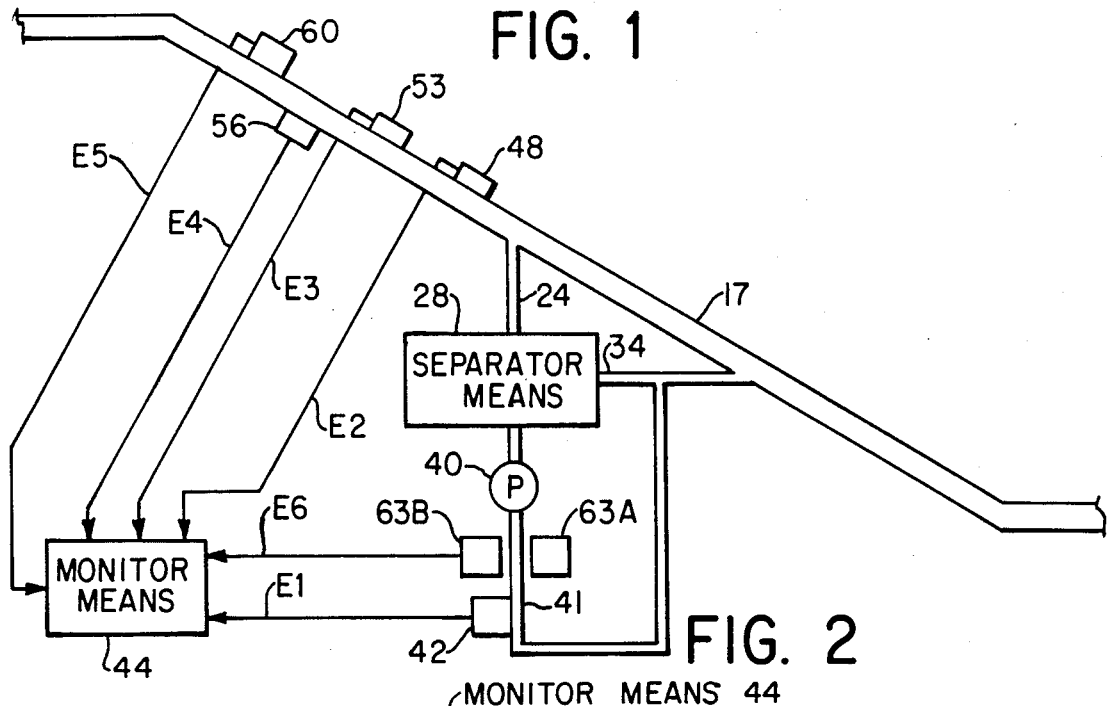
FIG. 1 is a graphical representation of a petroleum stream monitor constructed in accordance with the present invention monitoring a petroleum stream.

Referring to FIG. 1, the present invention monitors a crude oil production stream which normally includes not only the crude oil but water and gas. The crude oil production stream flows through a separating pipe 17. Pipe 17 is arranged so as to create a suitable angle of inclination to cause the production stream to separate into liquid and gas. A preferred angle of inclination lies within a range of angles between 10° and 60.

The liquid flow in pipe 17 is sampled by an inlet tubing 24 and provided to separator means 28. Separator means 28 separates substantially all gas that has not been separated in separating pipe 17 from the liquid and provides it by a return tubing 34 to separating pipe 17. The liquid may be applied to a mixer pump 40 where it is thoroughly mixed to achieve a homogeneous liquid and provided by another tubing 41 to return tubing 34.

A temperature sensor 42 senses the liquid temperature and provides a corresponding signal E1 to monitor means 44. A pressure sensor 48 senses the pressure and provides a pressure signal E2 to monitor means 44. Gas velocity measuring means 53, measures the velocity of the gas after stratification has taken place in separating pipe 17. Measuring means 53 provides a gas velocity signal E3 to monitor means 44. A liquid flow meter 56 measures the velocity of the liquid portion in separating pipe 17 and provides a corresponding signal E4 to monitor means 44. A conventional type densitometer 60 senses the density of the fluid in pipe 17 and provides a corresponding density signal E5 to monitor means 44. Microwave means 63A and 63B monitors the liquid in tubing 41 and provides signal E6 representative of the water cut of the liquid in line 41 to monitor means 44.

Figure 2:
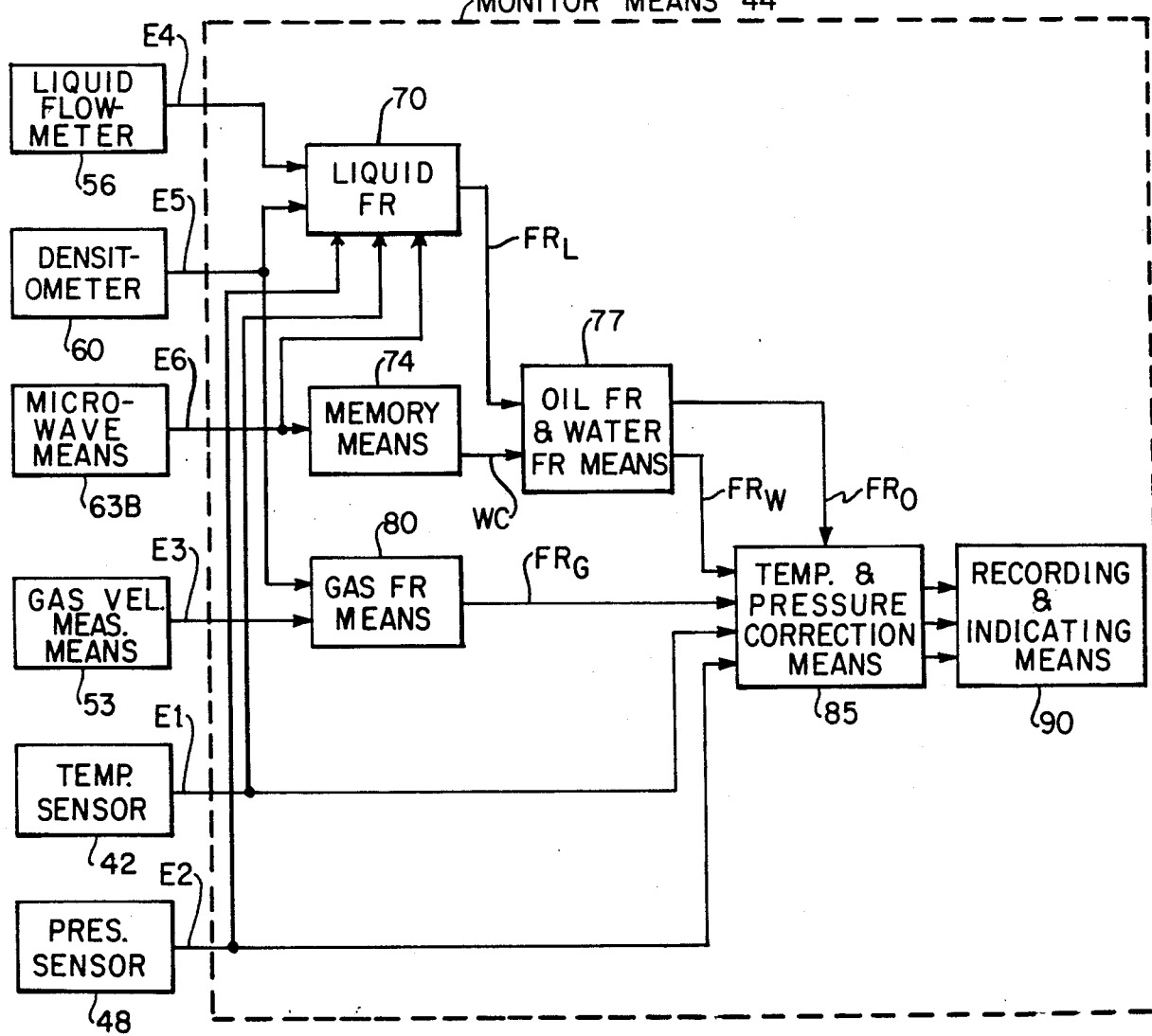
FIG. 2 is a simplified block diagram of a petroleum stream monitor constructed in accordance with the present invention.

With reference to FIG. 2, the signals E4, E5 provided by liquid flowmeter 56 and densitometer 60, respectively, are provided to liquid flow rate means 70 which provides a signal corresponding to the liquid flow $FR_L$ rate using the following equation:

$$FR_L = (A_L)(V_L),$$

where $A_L$ is the cross-sectional area of the liquid and $V_L$ is the velocity of the liquid represented by signal E4.

However, $A_L$ is not measured directly but requires the combining of signals E1, E2, E5, and E6 utilizing the following equations $$\bar{\rho} = (A_L/A)\rho_L + (1 - A_L/A)\rho_G$$

which is rewritten as $$A_L = (\bar{\rho} - \rho_G)A/(\rho_L - \rho_G)$$

where $\bar{\rho}$ is the average density of the petroleum stream measured by densitometer 60 and is represented by signal E5, $\rho_L$ is the density of the liquid represented by signal E6 from microwave means 63B and $\rho_G$ is the density of the gas which the known gas density from well tests corrected for temperature and pressure represented by signals E1 and E2 respectively.

Microwave means 63B provides signal E6 memory means contains lookup tables relating signal E6 amplitude to water cut values. Memory means 74 provides a signal Wc corresponding to the water cut of the liquid portion of the crude oil stream in accordance with signal E6. With signals $FR_L$ and Wc, oil flow rate and water flow rate means 77 determines the oil flow rate and the water flow rate and provides signals $FR_O$ and $FR_W$, respectively, accordingly. Signal E3 provided by gas velocity measuring means 53 and signal E5 from densitometer 60 are applied to gas flow rate means 80 which provides a signal $FR_G$ corresponding to the gas flow rate in accordance with the following equation:

$$FR_G = (A_G)(V_G),$$

where $A_G$ is the cross-sectional area of the gas represented by signal E5 and $V_G$ is the gas velocity represented by signal E3.

Signals $FR_W$ and $FR_O$ from the oil flow rate and water flow rate means 77 and signal $FR_G$ from the gas flow rate means 80 are provided to temperature and pressure correction means 85 receiving temperature signal E1 from temperature sensor 42 and pressure signal E2 from pressure sensor 48. Temperature and pressure correction means 85 adjusts signals $FR_O$, $FR_W$ and $FR_G$ so as to convert the oil flow rate, the water flow rate and the gas flow rate to standard condition flow rates. Correction means 85 provides standardized flow rate signals for the oil, water and gas to recording and indicating means 90 for their recordation and a corresponding display.

The present invention as hereinbefore described provides an indication and record of the gas flow rate, the oil flow rate and the water flow rates of a multiphase petroleum production stream. It would be obvious to one skilled in the art, that knowing the gas, oil and water flow rates one could also arrive at the volume by percent of these constituents.

What is claimed is:

1. Apparatus for monitoring a petroleum stream comprising:
    means for stratifying the petroleum stream into substantially liquid and gas streams,
    first means for sensing the parameters of the stratified petroleum stream and providing signals representative of the sensed parameters,
    means for sampling the liquid stream of the stratified petroleum stream to provide a sample stream,
    second means for sensing parameters of the sample stream and providing signals in accordance with the sensed parameters, and
    monitor means for providing signals representative of the water fraction, the gas fraction and the oil fraction of the petroleum stream in accordance with the signals from all the parameter sensing means.

2. Apparatus as described in claim 1 in which the first sensing means includes:
    means for determining the density of the petroleum stream and providing a corresponding signal,
    means for sensing the gas velocity of the gas stream of the stratified petroleum stream and providing a signal representative thereof,
    means for sensing the liquid velocity of the liquid stream of the stratified petroleum stream and providing a signal in accordance with the sensed liquid velocity, and
    means for sensing the pressure of the stratified petroleum stream and providing a signal corresponding to the sensed pressure.

3. Apparatus as described in claim 2 in which the sample means includes separator means for removing gas from the sample stream,
    means for returning the removed gas to the stratified petroleum stream, and
    means for returning the sample stream from the seperator means to the stratified petroleum stream.

4. Apparatus as described in claim 3 in which the second sensing means includes
    microwave means for monitoring the sample stream after it has left the separator means to provide a signal related to the water in the sample stream, and
    a sensor which senses the temperature of the sample stream after it leaves the separating means which provides a corresponding temperature signal.

5. Apparatus as described in claim 4 in which the monitor means includes liquid flow rate means connected to the density determining means, to the liquid velocity sensing means, to the pressure sensing means, to the microwave means and to the temperature sensor for providing a signal corresponding to the liquid flow rate in accordance with the signals from the density determining means, the liquid velocity sensing means, the pressure sensing means, the microwave means and the temperature sensor,
    memory means connected to the microwave means for providing a signal corresponding to the water content of the petroleum stream in accordance with the signal from the microwave means;
    gas flow rate means connected to the density sensing means and to the gas velocity sensing means for providing a signal corresponding to the gas flow rate of the petroleum stream in accordance with the signals from the density sensing means and the gas velocity sensing means; and
    oil/water flow means connected to the liquid flow rate means and to the memory means for providing signals corresponding to the water flow rate and to the oil flow rate in accordance with the signals from the liquid flow rate means and the memory means.

6. Apparatus as described in claim 5 in which the monitor means further includes signal processing means connected to the oil/water flow rate means, to the gas flow rate means, to the temperature sensing means, and to the pressure sensing means for providing temperature and pressure corrected signals corresponding to the flow rate of the gas, to the flow rate of the oil, and to the flow rate of the water.

7. Apparatus as described in claim 6 in which the stratifying means is means which cause the petroleum stream to flow at a predetermined angle to the horizontal so as to cause the liquid and gas to separate.

8. Apparatus as described in claim 1 in which the stratifying means is means which cause the petroleum stream to flow at a predetermined angle to the horizontal so as to cause the liquid and gas to separate.

9. Apparatus as described in claim 8 in which a preferred angle for petroleum stream flow lies within a range of angles between 10° and 60°.

10. A method for monitoring a petroleum stream comprising the steps of:
    stratifying the petroleum stream into substantially liquid and gas streams,
    sensing the parameters of the stratified petroleum stream and providing signals representative of the sensed parameters,
    sampling the liquid stream of the stratified petroleum stream to provide a sample stream,
    sensing parameters of the sample stream and providing signals in accordance with the sensed parameters, and
    providing output signals representative of the water fraction, the gas fraction and the oil fraction of the petroleum stream in accordance with the signals from all the parameter sensing steps.

11. A method as described in claim 10 in which the first mentioned sensing step includes:
    determining the density of the petroleum stream and providing a corresponding density signal,
    sensing the gas velocity of the gas stream of the stratified petroleum stream and providing a gas velocity signal representative thereof,
    sensing the liquid velocity of the liquid stream of the stratified petroleum stream and providing a liquid velocity signal in accordance with the senced liquid velocity, and
    sensing the pressure of the stratified petroleum stream and providing a corresponding pressure signal.

12. A method as described in claim 11 in which the sampling step includes:
    removing gas from the sample stream,
    returning the removed gas to the stratified petroleum stream, and
    returning the sample stream after the separator step to the stratified petroleum stream.

13. A method as described in claim 12 in which the sample stream sensing step includes:
    monitoring the sample stream after it has left the separator means using microwave devices to provide a water signal related to the water in the sample stream, and sensing the temperature of the sample stream after it leaves the separating means and providing a corresponding temperature signal.

14. A method as described in claim 13 in which the output signals step includes:
providing a liquid flow signal corresponding to the liquid flow rate in accordance with the density signal, the liquid velocity signal, the pressure signal, the water signal and the temperature signal,
providing a water content signal corresponding to the water content of the petroleum stream in accordance with the water signal,
providing a gas flow rate signal corresponding to the gas flow rate of the petroleum stream in accordance with the density signal and the gas velocity signal, and
providing a water flow rate signal and an oil flow rate signal corresponding to the water flow rate and to the oil flow rate, respectively, in accordance with the liquid flow rate signal and the water content signal.

15. A method as described in claim 14 in which the output signals step further includes providing temperature and pressure corrected signals corresponding to the flow rate of the gas, to the flow rate of the oil, and to the flow rate of the water in accordance with the oil flow rate signal, the water flow rate signal, the gas flow rate signal, the temperature signal and the pressure signal.

16. A method as described in claim 15 in which the stratifying step is accomplished by causing the petroleum stream to flow at a predetermined angle to the horizontal so as to cause the liquid and gas to separate.

17. A method as described in claim 10 in which the stratifying step is accomplished by causing the petroleum stream to flow at a predetermined angle to the horizontal so as to cause the liquid and gas to separate.

18. A method as described in claim 17 in which a preferred angle for stratifying the petroleum stream flow lies within a range of angles between 10° and 60°.

* * * * *